United States Patent [19]
Adolf et al.

[11] Patent Number: 5,250,167
[45] Date of Patent: Oct. 5, 1993

[54] ELECTRICALLY CONTROLLED POLYMERIC GEL ACTUATORS

[75] Inventors: Douglas B. Adolf; Mohsen Shahinpoor; Daniel J. Segalman; Walter R. Witkowski, all of Albuquerque, N. Mex.

[73] Assignee: The United States of America as represented by the United States Department of Energy, Washington, D.C.

[21] Appl. No.: 902,322

[22] Filed: Jun. 22, 1992

[51] Int. Cl.⁵ .............................................. B01D 7/34
[52] U.S. Cl. .......................... 204/299 R; 204/300 R; 204/180.1
[58] Field of Search ............ 204/299 R, 300 R, 180.1

[56] References Cited
U.S. PATENT DOCUMENTS 4,522,698  6/1985  Maget .............................. 204/299 R
5,100,933  3/1992  Tanaka et al. ....................... 524/555

Primary Examiner—John Niebling
Assistant Examiner—Kishor Mayekar
Attorney, Agent, or Firm—George H. Libman; Timothy D. Stanley

[57] ABSTRACT

Electrically controlled polymeric gel actuators or synthetic muscles capable of undergoing substantial expansion and contraction when subjected to changing pH environments, temperature, or solvent. The actuators employ compliant containers for the gels and their solvents. The gels employed may be cylindrical electromechanical gel fibers such as polyacrylamide fibers or a mixture of poly vinyl alcohol-polyacrylic acid arranged in a parallel aggregate and contained in an electrolytic solvent bath such as salt water. The invention includes smart, electrically activated devices exploiting this phenomenon. These devices are capable of being manipulated via active computer control as large displacement actuators for use in adaptive structure such as robots.

19 Claims, 4 Drawing Sheets

ELECTRICALLY CONTROLLED POLYMERIC GEL ACTUATORS

The United States Government has rights in this invention pursuant to Contract No. DE-AC04-76DP00789 between the Department of Energy and American Telephone and Telegraph Company.

BACKGROUND OF THE INVENTION

1. Field of the Invention

This invention relates to electrically controllable contractile/swelling synthetic muscles and robotic actuators and their method of operation. More particularly, this invention relates to encapsulated polyelectrolyte polymeric gels in electrolyic solutions capable of undergoing reversible expansion and contraction when appropriately stimulated, such as by an electric field in the range of a few volts per centimeter.

2. Description of the Prior Art

There are many computer-controlled actuators available for robotic and related applications. Examples of such actuators are PVDF actuators, piezoelectric actuators, such as PZT and Lithium-Niobate, electroheological (ER) fluid actuators such as glass sphere/silicone oil actuators. Other common actuators are linear motors, electro-magnetic actuators, hydraulic actuators, pneumatic actuators, and explosive-type actuators. These prior art actuators suffer from various disadvantages, such as size, complexity, high weight and weight/displacement, large power requirements, and high material costs.

It is known that certain co-polymers may be chemically contracted and expanded in electrolytic solutions by varying the degree of ionization of the solution, or the pH. As originally reported by W. Kuhn, B. Horgitay, A. Katchalsky and H. Eisenberg, "Reversible Dilation and Contration By Changing The State of Ionization of High-Polymer Acid Networks," Nature, Vol. 165, No. 4196, pp. 514-516, (1950) a three-dimensional network, consisting of polyacrylic acid can be obtained by heating a foil of polyacrylic acid containing a polyvalent alcohol such as glycerol or polyvinyl alcohol. The resulting three-dimensional networks are insoluble in water but swell enormously in water on addition of alkali, and contract enormously on addition of acids. Linear reversible dilations and contractions of the order of more than 400 percent have been been observed. Furthermore, the ultimate structural deformation (swelling or collapsing) of these gels is homogeneous in the sense that, for example, for a long cylindrical gel, the relative changes of the length and the diameter are the same. Similar properties are exhibited by polymethacrylic acid cross-linked cross-linked by divinyl benzene copolymerized in methanol.

The use of chemically stimulated pseudo-muscular actuation for chemomechanical engines and turbines was originally discussed by I. Z. Steinberg, A. Oplatka, and A. Katchalsky, "Mechano-Chemical Engines, Nature, Vol. 210, No. 5036, pp. 568-571, (1966). Applications of polyelectrolyte gels driven by solvent substitution is discussed by D. Caldwell and P. Taylor, "Chemically Stimulated Pseudo-Muscular Actuation," International Journal of Engineering Science, Vol. 28, No. 8, pp. 797-808, (1990).

The same effect can be obtained electrolytically. Application of a voltage across the polymer gel causes a pH gradient to evolve between the electrodes. For example, the polymeric fibers may be filled with platinum by alternatively treating them with solutions of platinic chloride and sodium borohydride. A reversible expansion and contraction of the fiber is obtained with the application of an electric field. Direct motion control of these polymeric muscles with position and velocity feedback is feasible. The behavior of polymeric gels in an electric field is discussed by T. Tanaka, I. Nishio, S. Sun and S. Ueno-Nishio, "Collapse of Gels in an Electric Field," Science, Vol. 218, pp 457-469, (1982). In principle, the devices of the prior art need have only one moving part, the actuating gel itself. There is not the attendant weight and complexity of electric motors or hydraulic pumps and actuators. All that is required is an electric field of the order of a few volts per centimeter. The major disadvantages of such devices are that, in general, the response times of these gels are much longer than conventional actuator components, and there is the inconvenience that the gel must be contained within a solvent bath.

The above-mentioned disadvantages are overcome in the present invention by containing the gel and its bath in a container. The novel devices of the present invention employ either rigid containers, or flexible and foldable membranes as required to confine the bath.

SUMMARY OF THE INVENTION

The present invention relates to electrically controlled polymeric gel actuators employing ionizable polymeric gels capable of undergoing substantial expansion and contraction when subjected to changing pH environments, temperature, or solvent. The novel actuators employ compliant containers for the gels and their solvents. These devices are capable of being manipulated via active computer control as large displacement actuators for use in adaptive structures such as robots.

It is a primary object of this invention to provide gel actuated devices or synthetic muscles useful as robotic actuators.

It is another object of this invention to provide gel actuated devices demonstrating compactness, simplicity, modest weight, small power requirements, and low material costs as compared to known robotic actuators It is still another object of this invention to provide gel actuated devices with improved response times.

It is still another object of this invention to provide gel actuated devices wherein the solvent bath is conveniently contained in a flexible container capable of flexing during operation of the actuator.

Additional objects, advantages, and novel features of the invention will become apparent to those skilled in the art upon examination of the following description or may be learned by practice of the invention. The objects and advantages of the invention may be realized and attained by means of the instrumentalities and combinations particularly pointed out in the appended claims.

To achieve the forgoing and other objects, and in accordance with the purpose of the present invention, as embodied and broadly described herein, the present invention may comprise fluid containment means for containment of an electrolytic solution, a first polymeric gel element disposed within said fluid containment means, means for introducing electric current through said solution having an anode and a cathode, and means for converting translation of at least a portion of said polymeric gel element into actuation external to said fluid containment means.

BRIEF DESCRIPTION OF THE DRAWINGS

The accompanying drawings, which are incorporated in and form part of the specification, illustrate embodiments of the present invention and, together with the description, serve to explain the principles of the invention.

DETAILED DESCRIPTION OF THE INVENTION

Figure 1:
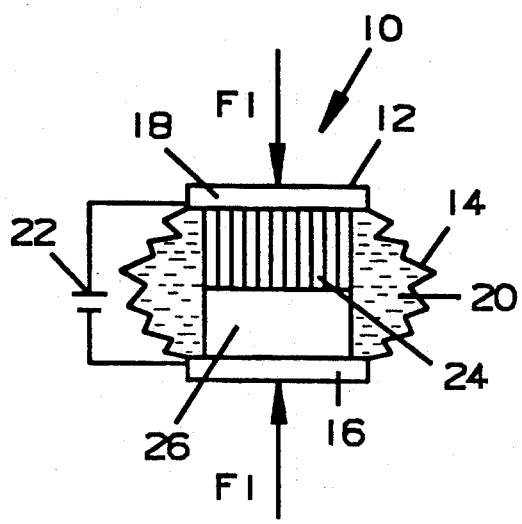
FIG. 1 is a schematic view in elevation of an encapsulated polymeric gel actuator employing a single cation-rich polyelectrolyte, the actuator being disposed in the contracted state.
Figure 1A:
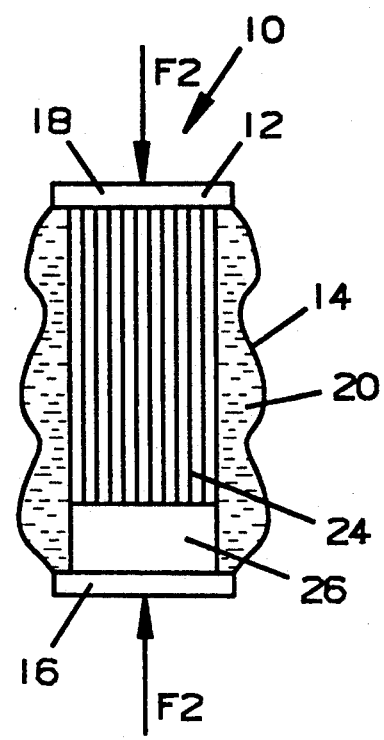
FIG. 1a is a schematic view in elevation of the encapsulated polymeric gel actuator of FIG. 1 disposed in the expanded state.

Referring to FIG. 1 and FIG. 1a, polymeric gel actuator 10 is shown in its contracted and expanded states, respectively, and includes hermetically sealed cylindrical shell structure 12, having a flexible wall 14 and end plates 16 and 18. Shell structure 12 contains an electrolytic solution 20 such as a 1.0 weight percent solution of NaCl in water. End plate 16 serves as a cathode and end plate 18 serves as an anode upon application of an electrical potential from power source 22. End plates 16 and 18 may be constructed of an appropriate conductive material such as platinum or gold. Motive power is provided by anion-rich polyelectrolyte polymeric gel 24. These gels may be cylindrical electromechanical gel such as polyacrylamide, or a mixture of polyvinyl alcohol-polyacrylic acid arranged in a parallel agreggate. They may be formed of integral structures or discrete fibers, as known in the art. Gel 24 is located within cylindrical shell 12 with one end attached to end plate 18 in any appropriate manner such as by stringing through holes or hooks formed in end plate 18. An inert spacer 26 is connected between cathode end plate 16 and the other ends of gel 24. Spacer 26 serves to keep fibers 24 ionically isolated from cathode end plate 16, as discussed hereinafter.

FIG. 1a shows a device 10 with gel 24 in the swollen or expanded state that results from absorption of solvent from the electrolyte. Upon application of electrical potential from power source 22, a pH gradient is formed within solution 20, causing gel 24 to release solvent and contract along their axis as shown in FIG. 1. The contraction of gel 24 pulls end plate 18 towards spacer 24. Any tensile force acting on end plates 16 and 18, such as F2 in FIG. 1a, becomes an increased tensile force F1 as in FIG. 1, thereby providing for actuation of any attached mechanism. The process can be reversed by removing electrical potential from end plates 16 and 18 or reversing polarity, thus, allowing gel 24 to absorb solvent from electrolyte 20 and expand back to the configuration of FIG. 1a, exerting tensile force F2.

Spacer 26 is a necessary component of the embodiment of FIG. 1. If fibers 24 were also connected directly to cathode 16, application of the the voltage from source 22 would cause the ends at cathode 16 to expand while the ends at anode 18 contract, resulting in no net mechanical force being applied between the electrodes.

The structure of this embodiment could also be reversed, with spacer 26 being between anode 18 and one ends of cation rich fibers; the other ends of these fibers being connected to cathode 16. In this reversed structure, application of a voltage would cause the fibers to absorb and cause the electrodes to move apart.

Figure 2:
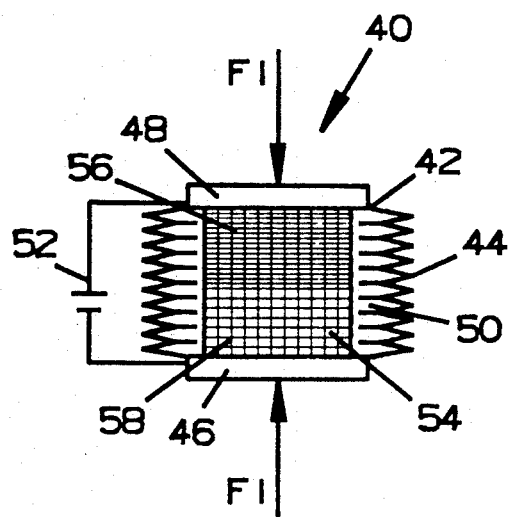
FIG. 2 is a schematic view in elevation of another embodiment of the encapsulated polymeric gel actuator of the invention employing both cation and anion-rich polyelectrolytes, the actuator being disposed in the contracted state.
Figure 2A:
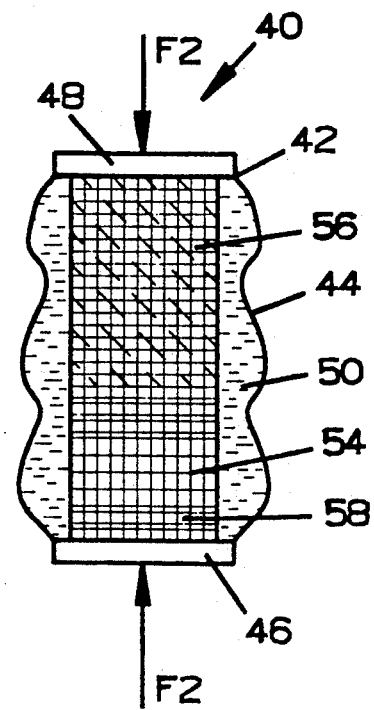
FIG. 2a is a schematic view in elevation of the encapsulated polymeric gel actuator of FIG. 3 disposed in the expanded state.

Referring to FIG. 2 and FIG. 2a, another embodiment of the invention is shown in which polymeric gel actuator 40, shown in its contracted and expanded states, respectively, includes hermetically sealed cylindrical shell structure 42 having a flexible wall 44 and end plates 46 and 48. Flexible wall 44 can have any desired form, but is illustrated in the form of a bellows-type structure made, for example, of a flexible, non-electrically conducting, material such as rubber. Shell structure 42 contains an electrolytic solution 50 similar to solution 20 of the previous embodiment. End plate 46 serves as a cathode and end plate 48 serves as anode upon application of an electrical potential from power source 52. An aggregate 54 of polyelectrolyte polymeric gels are located within cylindrical shell 42. Aggregate 54 is made up of anion-rich polyelectrolyte polymeric gel 56 in the vicinity of anode end plate 48 and cation-rich polyelectrolyte polymeric gel 58 in the vicinity of cathode end plate 46. Gels 56 and 58 are joined at a point about midway between end plates 46 and 48 within cylindrical shell 42, respectively, by means of direct union or attachment through intermediate means such as a bulkhead. The aggregate 54 is attached to end plates 46 and 48 in the manner described in the embodiment of FIG. 1.

The polymeric gel actuator of FIG. 2 and FIG. 2a operates in a similar manner to that of FIG. 1 and FIG. 1a in that gel aggregate 54 is in its expanded or swollen state in FIG. 2a without applied electric potential. Upon application of an electrical potential from power source 52, aggregate 54 contracts to the configuration of FIG. 2. Removal of electrical potential allows polymeric fiber aggregate 54 to expand to the state shown in FIG. 2a.

Figure 3:
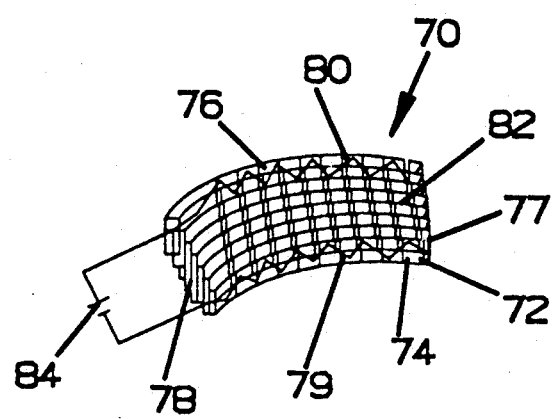
FIG. 3 is a perspective view of another embodiment of the invention wherein the encapsulated polymeric gel actuator is capable of flexing.

FIG. 3 is a schematic view of another embodiment of the present invention in which polymeric gel actuator 70 is in a bent configuration. This embodiment includes hermetically sealed planar flexible shell structure 72 having side walls 74 and 76 and end walls 77 and 78. Side wall 74 contains printed cathode 79, and side wall 76 contains printed anode 80. Sheets 82 of cation-rich polyelectrolyte polymeric gel are disposed within planar shell structure 72, attached at end walls 77 and 78. An electrolytic solution is contained within planar shell structure 72. Upon application of an electric potential from power source 84, polymeric gel actuator 70 changes from a rectangular configuration to the bent rectangle configuration of FIG. 3 as a result of the swelling of polymeric sheets 82 in the vicinity of cathode 79 and the contracting of polymeric sheets 82 in the vicinity of anode 80. Polymeric gel actuator 70 can be returned to the initial rectangular configuration by removing the electrical potential supplied by power source 84.

Figure 4:
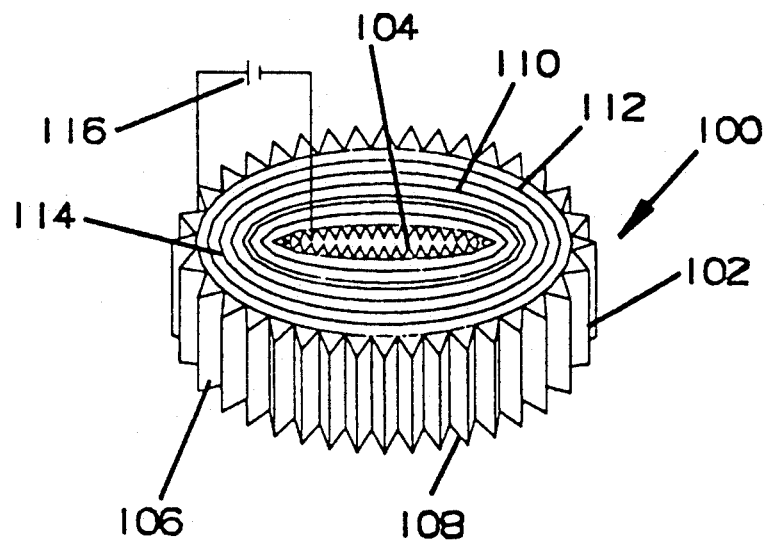
FIG. 4 is a view in perspective of another embodiment of the invention wherein the encapsulated polymeric gel actuator is capable of a sphinctering action.
Figure 4A:
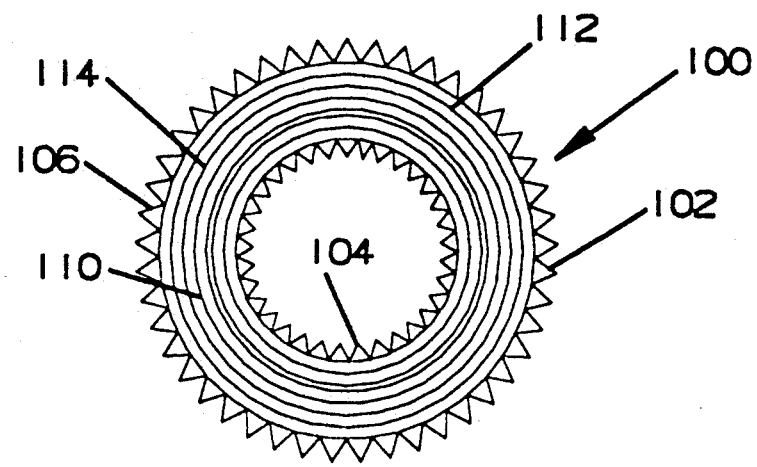
FIG. 4a is a plan view of the encapsulated polymeric gel actuator of FIG. 4.

Referring to FIG. 4 and FIG. 4a, there is shown an extension of the concept of the embodiment of FIG. 3 wherein polymeric gel actuator 100 is disposed in an annular form having hermetically sealed annular shell structure 102 having inner flexible wall 104 and outer flexible wall 106. The shell structure 102 is sealed by ends 108 and 110 The annular shell structure 102 contains electrolytic solution 112. Inner wall 104 forms a cathode and outer wall 106 forms an anode, and can be made of conducting elastic polymers, or contain electrodes printed thereon or attached thereto. Concentric sheets 114 of cation-rich polymeric gel material are disposed within annular shell structure 102. Upon application of an electrical potential from power source 116, polymer gel sheets 114 in the vicinity of inner wall 102 swell resulting in a sphincter type action opening of annular gel actuator 100. Upon removal of electrical potential, the cation-rich polymeric gel sheets contract to their original configuration resulting in the closing of the annular polymeric gel actuator 100. Proper actuation of a series of such annular actuators can result in a peristaltic pump action.

Figure 4B:
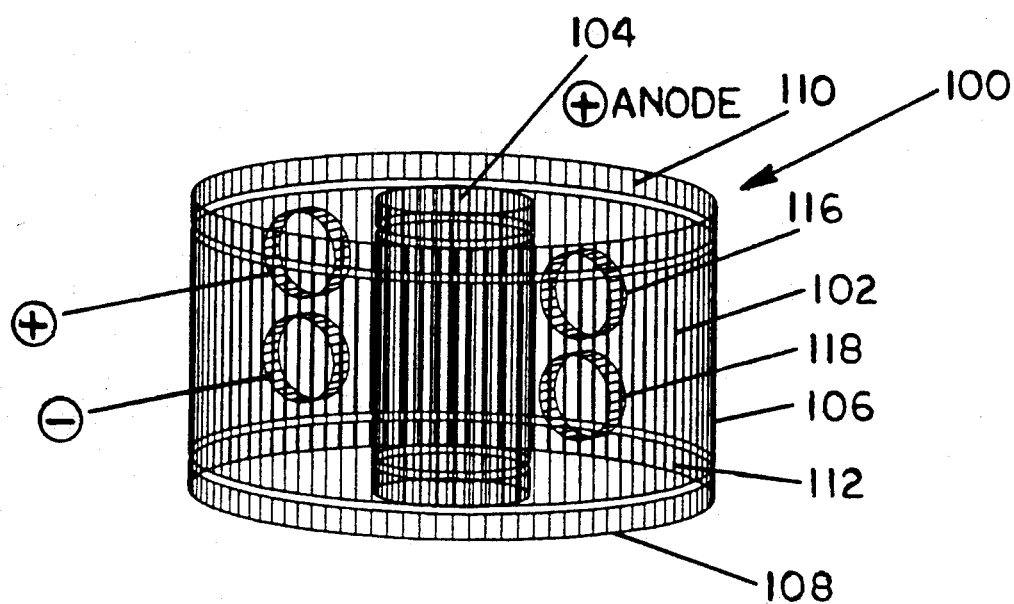
FIG. 4b is a view in perspective of an alternative embodiment of the invention of FIG. 4 wherein electrodes are placed in the upper and lower ends and torroidal polymer elements are located within the donut-shaped capsule.

Referring to FIG. 4b, there is shown an alternative annular actuator structure where end 110 forms an anode and end 108 forms a cathode. The polymeric gel is in the form of torroidal elements 116 and 118, concentric with inner wall 104. Element 116 is an anion-rich polyelectrolyte polymeric gel and element 118 is an cation-rich polyelectrolyte gel. Upon application of electric potential to electrodes 108 and 110, gel elements 116 and 118 contract against inner wall 104, closing the annulus. Upon removal of electrical potential, gel elements then expand allowing the annulus to open.

Figure 4C:
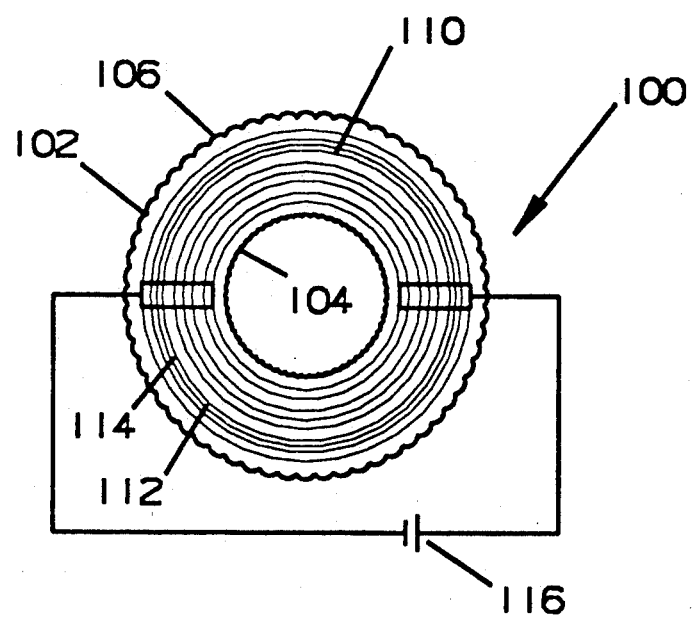
FIG. 4c is a plan view of the gel actuator of FIG. 4 showing alternative electrode placement within the capsule.

Referring to FIG. 4c, there is shown an alternative annular polymeric gel actuator structure wherein electrodes are disposed within the annular flexible shell structure 102 in diametrically opposed positions. Operation is otherwise similar to that of the embodiment of FIG. 4. The actuation of a series of electrodes can induce a peristaltic pump effect through progressive sphincter action of sets of electrodes within the same annular shell structure.

Figure 5:
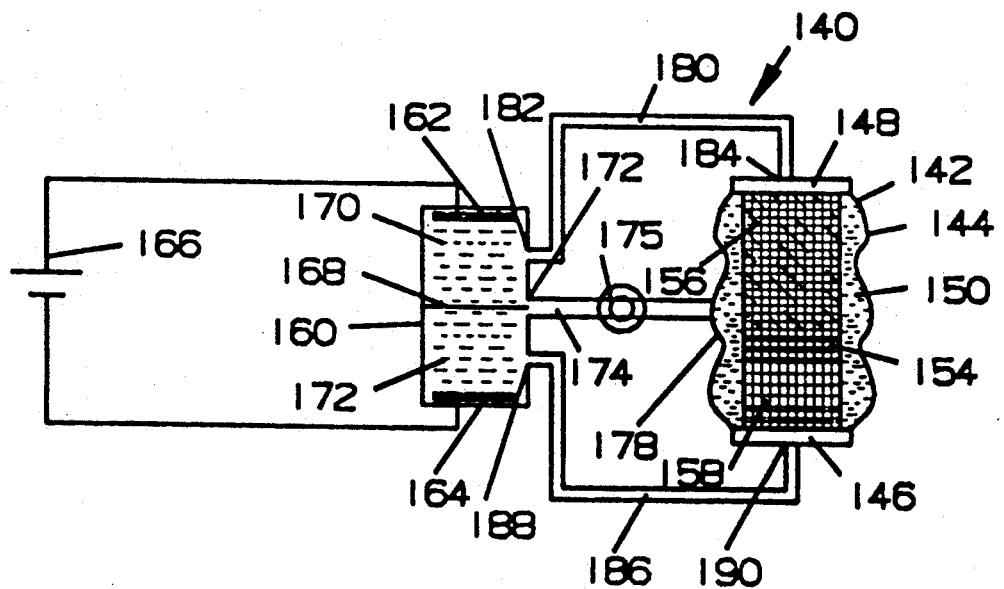
FIG. 5 is a schematic view in elevation of an another embodiment of the invention wherein actuating solvent is drawn from an electrolysis cell and introduced into the encapsulated polymeric gel actuator.

Referring to FIG. 5, there is shown another embodiment of the invention wherein a separate electrolysis cell and circulation system provides ionized electrolyte solution to a polymeric gel actuator similar to that of FIG. 2. Polymeric gel actuator 140 is shown in the swollen or expanded state and includes hermetically sealed shell structure 142, having a flexible wall 144 and opposite end plates 146 and 148. Cylindrical shell structure 142 contains an electrolytic solution 150. An aggregate 154 of polyelectrolyte polymeric gel fibers is located within cylindrical shell structure 152. Aggregate 154 is made up of anion-rich polyelectrolyte polymeric gel fibers 156 in the vicinity of end plate 148 and cation-rich polyelectrolyte polymeric gel fibers 158 in the vicinity of end plate 146. Fibers 156 and fibers 158 are joined and mounted to end plates 146 and 148 as described in the corresponding embodiment of FIG. 2 for fibers 56 and 58. A separate electrolysis cell 160 contains anode 162 and cathode 164 connected to power supply 166. Electrolysis cell 160 contains a permeable membrane 168 separating electrolysis cell 160 into an anode section 170 containing anode 162, and a cathode section 172 containing cathode 164. Conduit 174 containing pump 175 provides fluid communication of electrolysis cell 160 at cell connection 176 in the vicinity of permeable membrane 168 with cylindrical shell structure 142 in the vicinity of the joining point of gel fibers 156 and 158 at shell wall connection 178 in shell wall 144. Conduit 180 provides fluid communication of electrolysis cell 160 at anode section 170 at anode section connection 182 with shell 142 through end plate 148 at end plate connection 184. Conduit 186 provides fluid communication of electrolysis cell 160 at cathode section 170 at cathode section connection 188 with shell 142 through end plate 146 at end plate connection 190.

In operation, in order to obtain contraction of gel fiber aggregate 154 as in FIG. 2, neutral fluid is circulated by means of pump 175 from cylindrical shell 142 through conduit 174 into electrolysis cell 160 at cell connection 176, is ionized by means of electric potential supplied from power source 166 through anode 162 and cathode 164, and a low pH portion circulates from anode section 170 through conduit 180 into cylindrical shell 142 at end plate connection 184, a high pH portion being circulated from cathode section 172 through conduit 186 into cylindrical shell 142 at end plate connection 190. The low pH ionized solution from the anode section is supplied to the anion-rich polyelectrolyte polymeric gel fibers 146 and the high pH ionized solution from the cathode section is supplied to the cation-rich polyelectrolyte polymeric gel fibers 158 resulting in the contraction of fibers 156 and 158 of fiber aggregate 154, and resulting actuation of gel actuator 140 in the manner of gel actuator 40 of FIG. 2. Swelling or expansion of fiber aggregate 154 and, thus, gel actuator 140, can be obtained by stopping circulation of solution 150 for example by stopping pump 175, or shutting off power supply 166 and removing electric potential from electrolysis cell 160.

Figure 6:
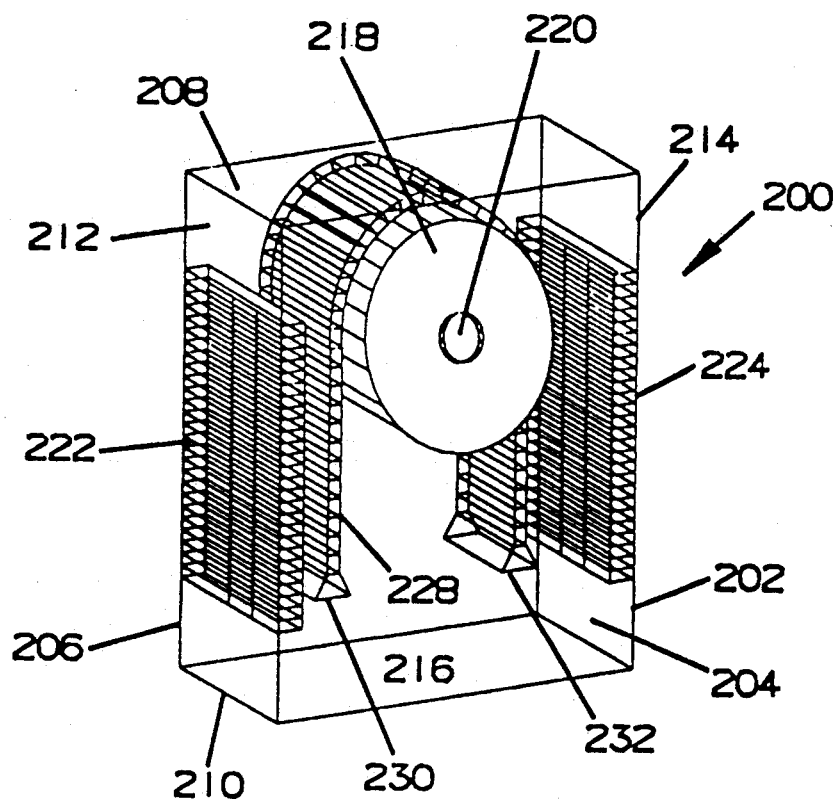
FIG. 6 is a view in perspective of another embodiment of the invention showing a polymeric gel driven motor/actuator having an output shaft.

Referring to FIG. 6, there is shown a polymeric gel motor/actuator 200 having closed inflexible shell structure 202 having front face 204, rear face 206, upper end 208, lower end 210, and opposite side walls 212 and 214, respectively. Contained within shell structure 202 is an electrolytic solution 216. A pulley 218 is located within shell structure 202 near upper end 208 and is mounted on axle 220 extending between front face 204 and rear face 206. A cathode 222 is disposed along side wall 212 and an anode 224 is disposed along side wall 214, each being located within the shell structure 202 so as to be in contact with electrolytic solution 216. Cathode 222 and anode 224 are connected with a power supply (not shown). A cation-rich polyelectrolyte polymeric gel belt 228 is disposed within shell structure 202 and attached at either end at mounts 230 and 232, respectively. Mounts 230 and 232 are mounted between front face 204 and rear face 206 so as to remain stationary relative to shell structure 202. Polymeric gel belt 228 is looped over pulley 218 so as to extend from mount 230 around pulley 218 and back to mount 232. Upon application of electrical potential from power source between cathode 222 and anode 224, polymeric gel belt 228 swells or expands in that portion in the vicinity of anode 224 and contracts in that portion in the vicinity of cathode 222 so as to impart rotation in pulley 218. Rotation of pulley 218 rotates axle 220 resulting in actuation through axle 220 to any desired mechanism. If an alternating current is applied by power source, an oscillating motion can be obtained in axle 220.

Cation-rich polyelectrolyte polymeric gels suitable for use in this invention can be prepared according to S. Katayama and A Ohate, Macromolecules, Vol. 18, p. 2782, (1985), and commercially available gels are suitable for treatment as previously discussed. Anion-rich polyelectrolyte polymeric gels suitable for use in the invention can be prepared according to T. Shiga and T. Kurauchi, Journal of Applied Polymer Science, Vol. 39, p. 2305, (1990) for polyacrylic acid/acrylamide, and Y. Osada, K. Umezowa, and A. Yamauchi, Bulletin of the Chemical Society of Japan, Vol. 67, p. 3232, (1989) for PAMPS. Also see U.S. Pat. No. 4,753,761 to Suzuki (1988) for methods of producing polymeric gels suitable for use in the present invention. While the invention contemplates the use of polymeric gel configurations such as sheets or solid shapes, aggregates of fibers of the order of 10-20 microns fiber diameter are preferred due to their high surface area and ready exposure to electrolytic solution, a construction that reduces response time.

A suitable electrolytic solution for use in the invention is a 1.0% by weight solution of salt, such as NaCl, in water. An electrical potential of about 2.0 volts per centimeter between electrodes is suitable for the practice of the invention. Suitable materials for construction of the walls of the container structure are polyethylene or Teflon. A suitable catalyst such as of platinum can be in the actuator container so as to combine any hydrogen and oxygen produced as a result of electolysis.

Because applied voltages will result in the generation of hydrogen and oxygen, a catalyst may be used in the cell to recombine these elements into water.

The particular sizes and equipment discussed herein are cited merely to illustrate a particular embodiment of this invention. It contemplated that the use of the invention may involve components having different sizes and shapes as long as the principle, the employment of polyelectrolyte polymeric gels in electrolytic solutions contained in flexible containers and selectively subjecting them to electrical potentials to induce desired expansion or contraction so as to act as an actuator or artificial muscle, is followed. The invention contemplates other derivative configurations including using conductive polyelectrolyte gel as an electrode, or other complex scheme involving anion-rich and cation-rich gels placed between electrodes in an electrolytic solution It is intended that the scope of the invention be defined by the claims appended hereto.

I claim:

1. A polymeric gel actuator comprising:
   fluid containment means for containment of an electrolytic solution;
   an electrolytic solution within said containment means;
   a first ionizable polymeric gel element disposed within said electrolytic solution;
   means for introducing electric current through said solution, said means having an anode and a cathode; and
   means for converting translation of at least a portion of said polymeric gel element into mechanical movement external to said fluid containment means;
   whereby, upon introduction of electric current through said solution, ions are formed therein which act upon said first polymeric gel element causing a change of dimensions of said polymeric gel element resulting in translation of said portion of said first polymeric gel element relative to another portion of said first polymeric gel element.

2. The polymeric gel actuator of claim 1, wherein said fluid containment means comprises flexible wall means.

3. The polymeric gel actuator of claim 2, wherein said fluid containment means further comprises first and second end means sealingly engaged with said wall means, said first polymeric gel element being so attached to said first and second end means such that translation of at least said portion of said polymeric gel element results in movement of one of said first and second end means relative to the other of said end means, thereby inducing displacement resulting in said external actuation.

4. The polymeric gel actuator of claim 3, wherein said anode and said cathode are located within said first and second end means, respectively.

5. The polymeric gel actuator of claim 4, further comprising spacing means so disposed within said fluid containment means as to ionically insulate one end of said gel element from one of said anode and cathode.

6. The polymeric gel actuator of claim 5, wherein said first polymeric gel element is an anion-rich polyelectrolyte and said spacing means is located in the vicinity of said second end means.

7. The polymeric gel actuator of claim 6, wherein said first polymeric gel element comprises a gel fiber bundle.

8. The polymeric gel actuator of claim 4, further comprising a second ionizable polymeric gel element disposed within said fluid containment means, said first polymeric gel element being attached to said first end means, said second polymeric gel element being attached to said second end means, said first and second polymeric gel elements being attached at a point intermediate between said first and said second end means, said first polymeric gel element being a cation-rich polyelectrolyte, said second gel element being an anion-rich polyelectrolyte.

9. The polymeric gel actuator of claim 8, wherein said first and said second polymeric gel elements comprise gel fiber bundles, respectively.

10. The polymeric gel actuator of claim 2, wherein said fluid containment means is in the form of a planar layer having first and second sides and first and second ends, said first side containing and anode disposed along its length, and said second side containing a cathode disposed along its length, said fluid containment means having a plurality of polymeric gel elements disposed therein, said polymeric gel elements being disposed in sheets located between said first and second ends and attached therebetween, said sheets being disposed substantially parallel to said sides.

11. The polymeric gel actuator of claim 10, wherein said plurality of gel elements are composed of anion-rich polyelectrolyte in the vicinity of said anode and of cation-rich polyelectrolyte in the vicinity of said cathode.

12. The polymeric gel actuator of claim 2, wherein said electrolytic fluid containment means is in the form of an annular container having concentric inner and outer flexible sides, a first end means, and a second end means, said inner side having a cathode disposed therein, said outer side having an anode disposed therein, said fluid containment means having a plurality of polymeric gel elements in the form of sheets disposed therein and concentric with said inner and outer sides and parallel thereto.

13. The polymeric gel actuator of claim 12, wherein said plurality of gel elements are composed of anion-rich polyelectroloytes in the vicinity of said anode and of cation-rich polyelectrolytes in the vicinity of said cathode resulting in a sphincter action of said polymeric gel actuator upon application of an electric potential to said means for introducing electric current.

14. The polymeric gel actuator of claim 13 wherein said anode and said cathode are disposed within said fluid containment means at substantially diametrically opposed positions.

15. The polymeric gel actuator of claim 14, further comprising a plurality cathode disposed parallel to a central axis of said annular containment means such that, upon timely application of electrical potential to said anode and cathode pairs, a peristaltic pump action is induced in said annular gel actuator.

16. The polymeric gel actuator of claim 1, further comprising an electrolysis cell, said electrolysis cell having an anode at a first end and a cathode at a second end, said electrolysis cell having a permeable membrane separating said cell into an anode section and a cathode section, said anode section being in fluid communication with said containment means at an end thereof by means of a first conduit means, said cathode section being in fluid communication with said containment means at an opposite end thereof by means of a second conduit means, said electrolysis cell being in fluid communication near said membrane with said containment means at a location midway between said opposite ends by means of a third conduit means, said third conduit means comprising pump means, whereby, upon application of electrical potential to said anode and said cathode, ion-rich solution flows from said anode section to said containment means through said first conduit means, oppositely charged ion-rich solution flows from said cathode section to said containment means through said second conduit means, and neutral solution flows from said containment means to said electrolysis cell through said third conduit means.

17. The polymeric gel actuator of claim 1, wherein said fluid containment means further comprises first and second opposing face means, first and second opposing end means, and first and second opposing side means, said first and second face means having an axle mounted therebetween and perpendicular thereto, and extending through one of said face means, said axle having a pulley mounted thereon within said containment means so as to e free to turn with said axle, said first polymeric gel element comprising a belt looped around said pulley, said belt having two ends attached to mounting means fixedly located within said containment means, said first and second side means having a cathode and an anode disposed thereon, said cathode and said anode being in communication with said solution and in the vicinity of opposite end portions of said belt, whereby, upon application of electric potential between said cathode and said anode, ion-rich solution causes one of said belt end portions to expand and the other of said end portions to contract, thus, inducing rotation of said axle by said pulley.

18. The polymeric gel actuator of claim 2, wherein said fluid containment means is in the form of an annular container having concentric inner and outer flexible sides, a first end means and a second end means, said first end means having an anode disposed therein, said second end means having a cathode disposed therein, said first polymeric gel element being in the shape of a torroid and being located within said annular container in the vicinity of said anode and concentric with said inner side, said first gel element being a cation-rich polyelectrolyte, a second polymeric gel element similar in shape to said first gel element located within said annular container in the vicinity of said cathode and concentric with said inner side, said second gel element being an anion-rich polyelectrolyte, whereby, upon application of electrical potential between said anode and said cathode, ion-rich solution causes said first and second gel elements to contract against said inner side, causing the annulus to close in a sphincter-type action, said first and second gel elements expanding upon removal of electrical potential to allow opening of the annulus.

19. The polymeric gel actuator of claim 18, wherein said first and second gel elements are composed of gel fiber bundles.

* * * * *